United States Patent
Lim et al.

(10) Patent No.: US 9,925,756 B2
(45) Date of Patent: Mar. 27, 2018

(54) SUBSTRATE PEELING DEVICE, METHOD FOR PEELING SUBSTRATE, AND METHOD FOR FABRICATING FLEXIBLE DISPLAY DEVICE

(71) Applicant: SAMSUNG DISPLAY CO., LTD., Yongin-si, Gyeonggi-do (KR)

(72) Inventors: Hyung Chul Lim, Asan-si (KR); Young Gu Kim, Asan-si (KR); Hyun Jun Cho, Asan-si (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 0 days.

(21) Appl. No.: 15/405,933

(22) Filed: Jan. 13, 2017

(65) Prior Publication Data
US 2017/0120571 A1 May 4, 2017

Related U.S. Application Data

(62) Division of application No. 14/093,193, filed on Nov. 29, 2013.

(30) Foreign Application Priority Data

Mar. 11, 2013 (KR) .................. 10-2013-0025733
Nov. 28, 2013 (KR) .................. 10-2013-0146379

(51) Int. Cl.
*B32B 38/10* (2006.01)
*B32B 43/00* (2006.01)
(Continued)

(52) U.S. Cl.
CPC .......... *B32B 43/006* (2013.01); *B23K 26/009* (2013.01); *B23K 26/032* (2013.01);
(Continued)

(58) Field of Classification Search
CPC . B32B 38/10; B32B 43/006; Y10T 156/1158; Y10T 156/1917; B23K 26/009;
(Continued)

(56) References Cited

U.S. PATENT DOCUMENTS 5,414,510 A  5/1995 Schultz et al.
7,923,065 B2 * 4/2011 Murakami ............ G03G 21/00
                                              118/261
(Continued)

OTHER PUBLICATIONS

Office Action dated Jul. 7, 2017 in corresponding European Patent Application No. 13198260.5 which was filed Dec. 19, 2013.

*Primary Examiner* — Mark A Osele
*Assistant Examiner* — Nickolas Harm
(74) *Attorney, Agent, or Firm* — F. Chau & Associates, LLC

(57) ABSTRACT

A method for fabricating a display device is provided. A laser having a power density is provided to a substrate coupling body. The substrate coupling body includes a first substrate and a second substrate coupled to the first substrate. The second substrate is separated from the first substrate. An optical property of the first substrate separated from the second substrate is measured. The power density of the laser is adjusted based on the optical property of the first substrate.

18 Claims, 13 Drawing Sheets

(51) Int. Cl.
| | |
|---|---|
| *H01L 21/683* | (2006.01) |
| *H01L 21/66* | (2006.01) |
| *H01L 51/00* | (2006.01) |
| *H01L 27/12* | (2006.01) |
| *B23K 26/00* | (2014.01) |
| *B23K 26/03* | (2006.01) |
| *B23K 26/06* | (2014.01) |
| *G01N 21/59* | (2006.01) |
| *H01L 27/32* | (2006.01) |
| *G02F 1/1368* | (2006.01) |
| *G02F 1/1333* | (2006.01) |
| *B23K 26/362* | (2014.01) |

(52) U.S. Cl.
CPC ......... *B23K 26/0626* (2013.01); *G01N 21/59* (2013.01); *H01L 21/6835* (2013.01); *H01L 22/20* (2013.01); *H01L 27/1218* (2013.01); *H01L 27/1259* (2013.01); *H01L 51/003* (2013.01); *H01L 51/0031* (2013.01); *H01L 51/0097* (2013.01); *B23K 26/362* (2013.01); *B32B 38/10* (2013.01); *B32B 2310/0843* (2013.01); *B32B 2457/20* (2013.01); *G02F 1/1368* (2013.01); *G02F 1/133305* (2013.01); *H01L 27/3244* (2013.01); *H01L 2221/68386* (2013.01); *H01L 2227/326* (2013.01); *H01L 2251/5338* (2013.01); *Y10T 156/1158* (2015.01); *Y10T 156/1917* (2015.01)

(58) Field of Classification Search
CPC .............. B23K 26/032; B23K 26/0626; B23K 26/362; G10N 21/59
USPC .................................. 156/712, 753; 73/655
See application file for complete search history.

(56) References Cited

U.S. PATENT DOCUMENTS

| | | |
|---|---|---|
| 2006/0237406 A1 | 10/2006 | Schmidt-Sandte et al. |
| 2007/0292632 A1 | 12/2007 | Yoshida |
| 2009/0225160 A1 | 9/2009 | Shah et al. |
| 2009/0296774 A1 | 12/2009 | Koelmel et al. |
| 2010/0139406 A1 | 6/2010 | Stievater et al. |
| 2010/0210055 A1* | 8/2010 | Yoon ................... H01L 27/1266 438/30 |
| 2011/0130073 A1 | 6/2011 | Furukawa et al. |
| 2011/0204361 A1* | 8/2011 | Nishiki ................. H01L 21/268 257/52 |
| 2011/0290406 A1* | 12/2011 | Dang ................. H01L 21/6835 156/155 |
| 2012/0258605 A1 | 10/2012 | Wagner |
| 2013/0014905 A1 | 1/2013 | Nakazawa et al. |
| 2013/0193122 A1* | 8/2013 | Nomaru ........... H01L 21/76898 219/121.62 |
| 2014/0251533 A1 | 9/2014 | Lim et al. |
| 2014/0251546 A1* | 9/2014 | Deguchi ........... H01L 21/67092 156/702 |

\* cited by examiner

SUBSTRATE PEELING DEVICE, METHOD FOR PEELING SUBSTRATE, AND METHOD FOR FABRICATING FLEXIBLE DISPLAY DEVICE

CROSS-REFERENCE TO RELATED APPLICATIONS

This application is a divisional of U.S. application Ser. No. 14/093,193 filed Nov. 29, 2013, which claims priority under 35 U.S.C. 119 to Korean Patent Application No. 10-2013-0025733, filed on Mar. 11, 2013 in the Korean Intellectual Property Office, and Korean Patent Application No. 10-2013-0146379, filed on Nov. 28, 2013 in the Korean Intellectual Property Office, the entire contents of both disclosures are incorporated by reference herein.

BACKGROUND

1. Technical Field

The present invention relates to a substrate peeling device, a method for peeling a substrate, and a method for manufacturing a flexible display device, and more particularly to a substrate peeling device using a laser, a method for peeling a substrate, and a method for fabricating a flexible display device.

2. Discussion of Related Prior Art

When flexible display devices are fabricated, carrier substrates are used to support a structure of flexible display devices while the structure of the flexible display devices is manufactured. The carrier substrates are relatively less flexible. After completing the structure of the flexible display devices, the carrier substrates are separated from the structure of the flexible display devices using a substrate peeling device. The substrate peeling device is used to separate the structure of the flexible devices from the carrier substrates using a laser.

SUMMARY

According to an exemplary embodiment of the present invention, a method for fabricating a display device is provided. A laser having a power density is irradiated on a substrate coupling body. The substrate coupling body includes a first substrate and a second substrate coupled to the first substrate. The second substrate is separated from the first substrate. An optical property of the first substrate separated from the second substrate is measured. The power density of the laser is adjusted based on the optical property of the first substrate.

According to an exemplary embodiment of the present invention, a method for fabricating a display device is provided. A laser having a power density is irradiated on a substrate coupling body. The substrate coupling body includes a first substrate and a second substrate coupled to the first substrate. A reflection ratio of the substrate coupling body is measured. The first substrate and the second substrate are separated from each other. The power density of the laser is adjusted based on the reflection ratio.

According to an exemplary embodiment of the present invention, a substrate peeling device includes a laser irradiation unit and an optical property detection unit. The laser irradiation unit is configured to generate a laser having a power density and to irradiate the laser on a substrate coupling body. The substrate coupling body includes a first substrate and a second substrate coupled to the first substrate. The optical property detection unit is configured to measure an optical property of the first substrate separated from the second substrate using the laser. The power density of the laser is adjusted based on the optical property of the first substrate.

According to an exemplary embodiment of the present invention, a substrate peeling device includes a laser irradiation unit and an optical property detection unit. A laser irradiation unit is configured to irradiate a laser having a power density on a substrate coupling body. The substrate coupling body includes a first substrate and a second substrate coupled to the first substrate. The optical property detection unit is configured to measure a light reflection ratio of the substrate coupling body. The power density of the laser is adjusted based on the light reflection ratio of the substrate coupling body.

BRIEF DESCRIPTION OF THE DRAWINGS

These and other features of the present invention will become more apparent by describing in detail exemplary embodiments thereof with reference to the accompanying drawings of which.

DETAILED DESCRIPTION OF THE EMBODIMENTS

Figure 1:
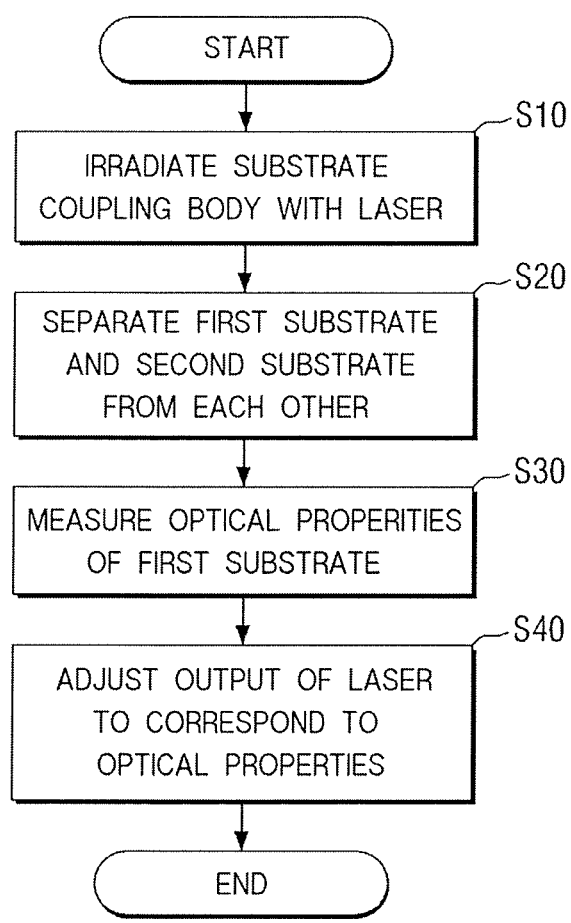
FIG. 1 is a flowchart illustrating a method for peeling a substrate according to an exemplary embodiment of the present invention.

Exemplary embodiments of the present invention will be described below in detail with reference to the accompanying drawings. However, the inventive concept may be embodied in different forms and should not be construed as limited to the embodiments set forth herein. In the drawings, the thickness of layers and regions may be exaggerated for clarity. It will also be understood that when a layer is referred to as being "on" another layer or substrate, it may be directly on the other layer or substrate, or intervening layers may also be present. Like reference numerals may refer to the like elements throughout the specification and drawings.

Hereinafter, embodiments of the present invention will be described with reference to the drawings.

FIG. 1 is a flowchart illustrating a method for peeling a substrate according to an exemplary embodiment of the present invention. Referring to FIG. 1, a method for peeling a substrate includes irradiating a substrate coupling body with a laser having a predetermined power density (S10), separating the substrate coupling body into a first substrate and a second substrate (S20), measuring an optical property of the first substrate (S30), and adjusting an output of the laser based on the measured optical property (S40). The method for peeling a substrate of FIG. 1 may be performed by a substrate peeling device. Hereinafter, referring to FIG. 2, the substrate peeling device will be described. The output of the laser may include intensity or a power density of the laser. The laser may be provided in a form of a laser beam.

Figure 2:
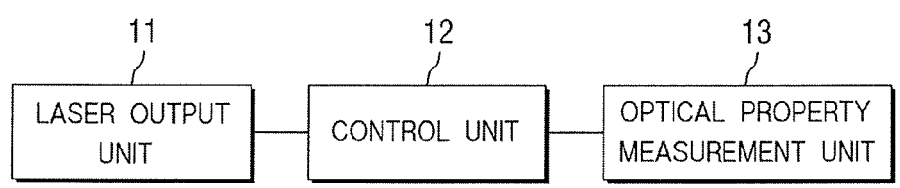
FIG. 2 is a block diagram illustrating a substrate peeling device according to an exemplary embodiment of the present invention.

FIG. 2 is a block diagram of a substrate peeling device according to an embodiment of the present invention. A substrate peeling device 10 includes a laser output unit 11, a control unit 12, and an optical property measurement unit 13.

The laser output unit 11 may generate the laser and provide the laser to the substrate coupling body. The laser is irradiated onto the substrate coupling body, and reduces a coupling force between the first substrate and the second substrate to facilitate the peeling of the substrate. The output of the laser that is generated by the laser output unit 11 may be adjusted.

The control unit 12 may control the laser output unit 11 to adjust the output of the laser generated by the laser output unit 11. For example, the control unit 12 may control the laser output unit 11 based on an optical property of the first substrate measured by the optical property measurement unit 13. In an exemplary embodiment, the laser output unit 11 may be manually controlled based on the optical property of the first substrate measured by the optical property measurement unit 13.

The optical property measurement unit 13 may measure the optical property of the substrate coupling body after or before the substrate is peeled. The optical property may include a light permeability, a light reflection ratio, or a retro reflection ratio, but are not limited thereto. The optical property measured by the optical property measurement unit 13 may relate to the output of the laser generated from the laser output unit 11. The details thereof will be described later with reference to FIGS. 7, 10, and 13. The substrate peeling device 10, which includes the optical property measurement unit 13, may determine the degree of the output of the laser based on the measured optical property, and may adjust the output of the laser at an appropriate level based on the measured optical property of the optical property measurement unit 13. If the output of the laser is excessive, the substrate coupling body, which are irradiated with the laser, may be damaged, whereas if the output of the laser is insufficient, the peeling of the substrate might not be appropriately performed. The substrate peeling device 10 may make the peeling of the substrate without causing some damage on the substrate coupling body by adjusting the output of the laser at an appropriate level.

Figure 3:
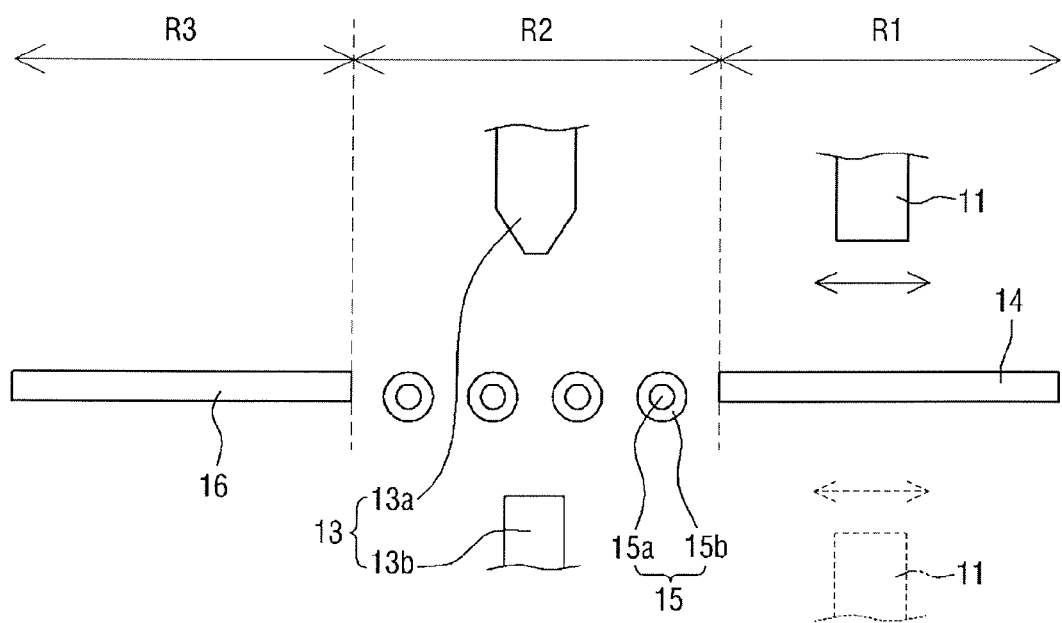
FIG. 3 is a side view of a substrate peeling device according to an exemplary embodiment of the present invention.

Hereinafter, referring to FIG. 3, the substrate peeling device 100 will be described in more detail. Referring to FIG. 3, the substrate peeling device 10 includes a peeling region R1, a conveyance region R2, and a loading region R3.

In the peeling region R1, the substrate coupling body may be peeled. For example, the substrate coupling body may be divided into a first substrate and a second substrate. For example, the first substrate may include a transparent glass substrate, and the second substrate may include a flexible display. The substrate peeling device 10 further includes a first stage 14. The first stage 14 is arranged in the peeling region R1 together with the laser output unit 11. The substrate coupling body is placed on the first stage 14, and the laser output unit 11 provides a laser to the substrate coupling body to separate the substrate coupling body into the first substrate and the second substrate. In an exemplary embodiment, the laser output unit 11 may be arranged over the first stage 14, and provide the laser to the substrate coupling body as it moves in a horizontal direction. In other embodiments, the laser output unit 11 may be arranged under the first stage 14, and provide the laser to the substrate coupling body as it moves in a horizontal direction. The first stage 14 may include a transparent material to transmit the laser L.

The first substrate, which is separated from the second substrate in the peeling region R1, may be conveyed to the loading region R3 through the conveyance region R2. The substrate peeling device 10 further includes a roller 15 arranged in the conveyance region R1 together with the optical property measurement unit 10. The roller 15 may convey the first substrate from the peeling region R1 to the loading region R3. The roller 15 may include a plurality of rotating shafts 15a that extend in the horizontal direction and a plurality of contact members 15b arranged in the circumferences of the rotating shafts 15a. The rotating shafts 15a may receive a rotating force from a power providing means (not illustrated) to be rotated. The contact members 15b may come in contact with the first substrate that is conveyed by the conveyance means 15, and may convey the first substrate through transferring the rotating force of the rotating shafts 15a to the first substrate. The contact members 15b may include an elastic material to protect the first substrate. The transferring of the first substrate is not limited to using the roller 15. For example, the first substrate may be transferred using a conveyance arm.

The optical property measurement unit 13 includes a light irradiation unit 13a and a light receiving unit 13b. The light irradiation unit 13*a* is arranged over the roller 15, and the light receiving unit 13*b* is arranged under the roller 15. However, the arrangement of the light irradiation unit 13*a* and the light receiving unit 13*b* may vary according to exemplary embodiments. The optical property measurement unit 13 may measure the optical property of the first substrate that is conveyed by the roller 15 after the first substrate is separated from the substrate coupling body. In an exemplary embodiment, when the optical property measurement unit 13 measures the optical property of the first substrate, the roller 15 may stop the first substrate so that the optical property measurement unit 13 measures the optical property of the first substrate in a state where the first substrate is stopped. The details of the optical property measurement unit 13 will be described later with reference to FIGS. 6 and 7.

The first substrate may be loaded in the loading region R3 through the roller 15. The substrate peeling device 10 further includes a second stage 16, and the second stage 16 is arranged in the loading region R3. On the second stage 16, the first substrate is loaded after the optical property of the first substrate is measured.

Figure 4:
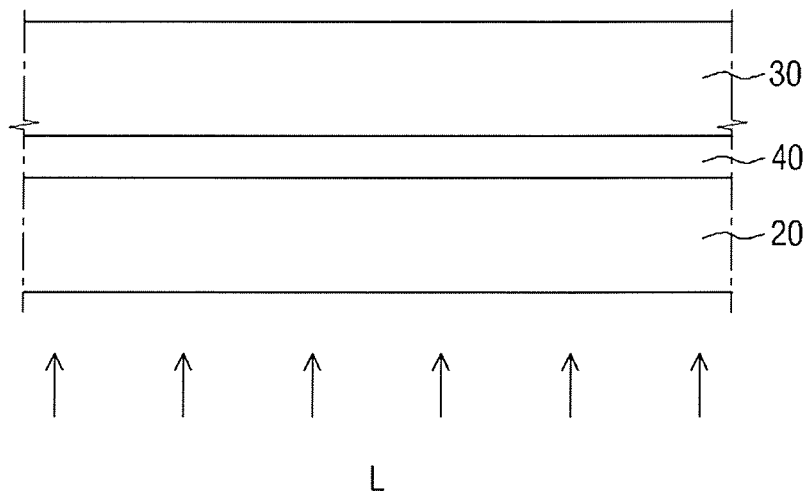
FIG. 4 is a cross-sectional view illustrating a substrate coupling body to which a laser is provided according to an exemplary embodiment of the present invention.
Figure 5:
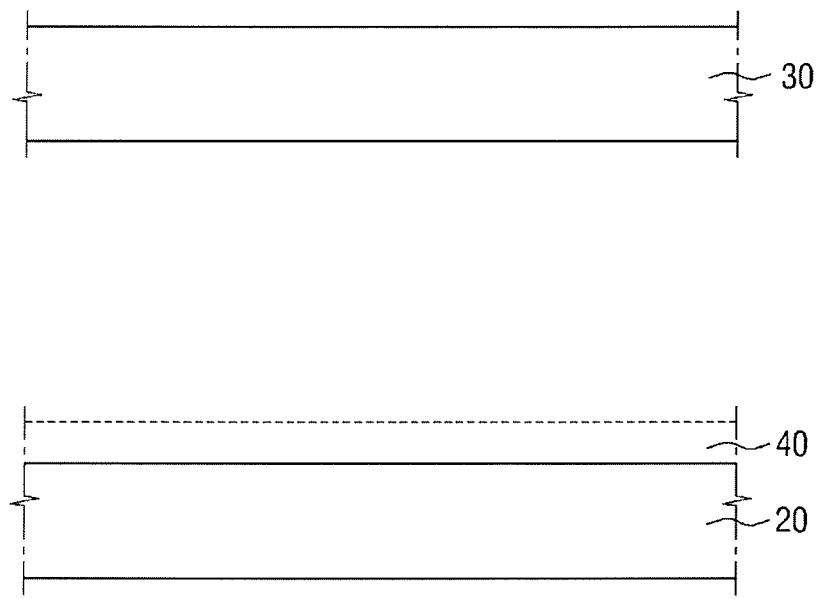
FIG. 5 is a cross-sectional view illustrating a first substrate and a second substrate separated from each other according to an exemplary embodiment of the present invention.
Figure 6:
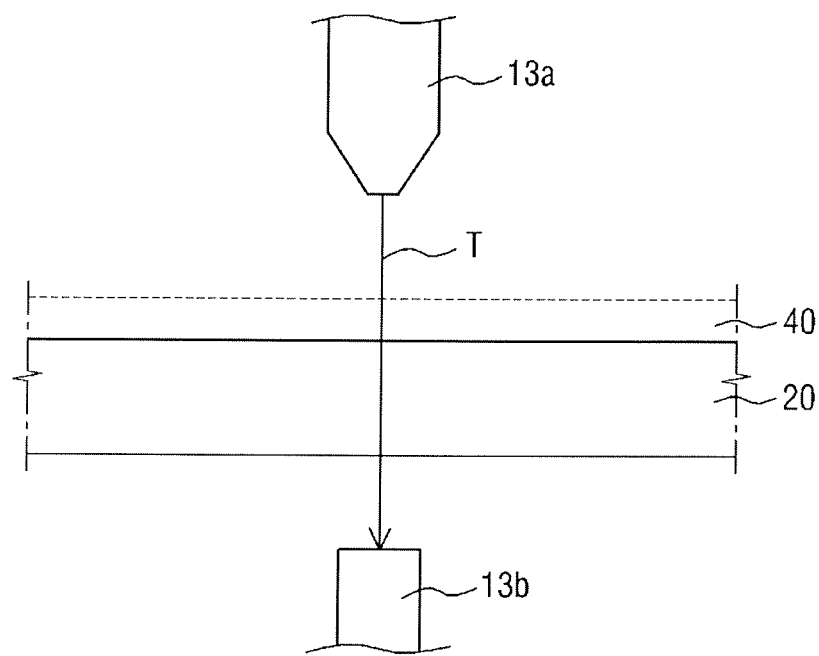
FIG. 6 is a view illustrating an arrangement for measuring an optical property of a first substrate according to an exemplary embodiment of the present invention.
Figure 7:
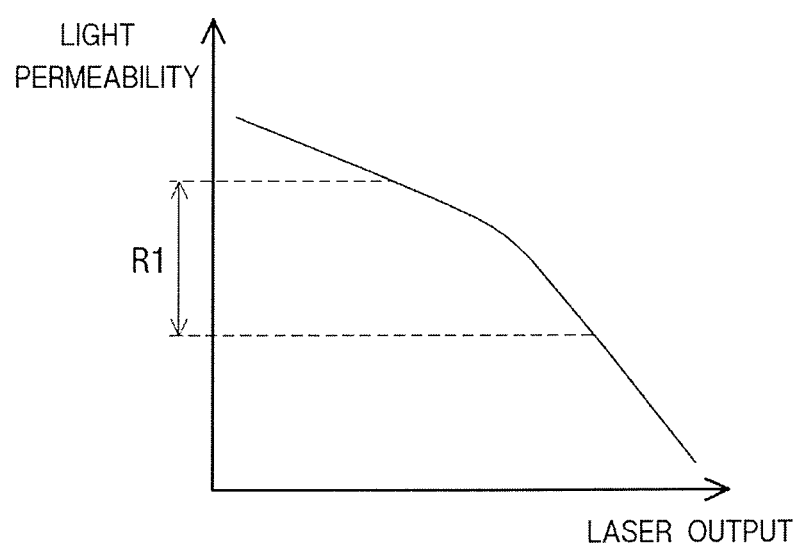
FIG. 7 is a graph illustrating a relationship between an intensity of a laser and a light permeability according to an exemplary embodiment of the present invention.

Hereinafter, referring to FIGS. 1 to 7, a method for peeling a substrate according to an exemplary embodiment of the present invention will be described. FIG. 4 is a cross-sectional view of a substrate coupling body which is irradiated by a laser L according to an exemplary embodiment of the present invention. FIG. 5 is a cross-sectional view of a first substrate and a second substrate after the substrate coupling body having been separated into the first substrate 20 and the second substrate 30 according to an exemplary embodiment of the present invention. FIG. 6 is a view illustrating measuring an optical property of the first substrate 20 according to an exemplary embodiment of the present invention. FIG. 7 is a graph illustrating a relationship between a laser output provided to the substrate coupling body and a light permeability of the first substrate 20 according to an exemplary embodiment of the present invention.

In S10, the substrate coupling body is irradiated with the laser L while the substrate coupling body is placed on the first stage 14. The substrate coupling body includes a first substrate 20 and a second substrate 30. The first substrate 20 may include a material that is optically transparent and transmit the laser L. For example, the first substrate 20 may include glass. The first substrate 20 may have a relatively lower degree of flexibility than the second substrate 30. The first substrate 20 may serve as a carrier substrate by supporting the second substrate 30, but is not limited thereto.

The second substrate 30 is arranged on the first substrate 20. The second substrate 30 is attached to the first substrate 20. The second substrate 30 may include a flexible substrate, but is not limited thereto. In addition, the second substrate 30 may include pixels arranged on the flexible substrate.

Specifically, the second substrate 130 may include a flexible substrate, a thin film transistor layer arranged on the flexible substrate, and a display layer connected to the thin film transistor layer.

The flexible substrate may include a material including kapton, polyethersulphone (PES), polycarbonate (PC), polyimide (PI), polyethyleneterephthalate (PET), polyethylenenaphthalate (PEN), polyacrylate (PAR), or fiber reinforced plastic (FRP), but is not limited thereto.

The thin film transistor layer may include thin film transistors and wirings for driving the thin film transistors. The thin film transistors may be connected to the display layer to control the display layer, and thus an image may be displayed on the display layer of the flexible display device.

The display layer may be connected to the thin film transistor layer. The display layer may be arranged on the thin film transistor layer. The detailed configuration of the display layer may vary depending on the kind of the flexible display device. The flexible display device may include an organic light emitting display device, a liquid crystal display device, or an electrophoretic display, but is not limited thereto. For example, if the flexible display device is an organic light emitting display device, the display layer may include an organic light emitting layer arranged between a cathode electrode and an anode electrode. Further, if the flexible display device is a liquid crystal display device, the display layer may include a first electrode and a second electrode to form an electric field therebetween, and may also include a liquid crystal layer that includes liquid crystal molecules of which the arrangement is changed by the electric field formed between the first electrode and the second electrode.

The substrate coupling body further includes the adhesive layer 40. The adhesive layer 40 is arranged between the first substrate 20 and the second substrate 30. The adhesive layer 40 may serve to assist the coupling between the first substrate 20 and the second substrate 30. The adhesive layer 40 may include a material that is optically transparent or that transmits at least the laser L. The adhesive layer 40 may have a high thermal resistance. For example, the adhesive layer 40 may have a glass transition temperature equal to or 220° C. higher than that of the first substrate 20. For example, the adhesive layer 40 may include silicon or acrylic polymer adhesives. In the case that the adhesive layer 40 includes polysilicon, the adhesive layer 40 has a glass transition temperature equal to or 220° C. higher than the first substrate 20. The polysilicon that is used as the adhesive layer 40 may include PDMS (polydimethylsiloxane) having silicon oxide as a main component, and this may be used together with silica nanopowder. The adhesive layer 40 may be formed on the first substrate 20 in a printing method, a slit coating method, a spin coating method, or a dipping method.

In an exemplary embodiment, the adhesive layer 40 may be omitted and the first substrate 20 may be directly coupled to the second substrate 30 without the adhesive layer 40. The base substrate of the second substrate 20 may be formed by depositing or coating the base material on the first substrate 30. The first substrate 20 and the second substrate 30 may be coupled to each other physically or chemically at the interface between the first substrate 20 and the second substrate 30. The coupling force between the first substrate 20 and the second substrate 30 may be enhanced by heat treatment process.

The laser L is provided from the laser output unit 11 to the substrate coupling body. The laser L may be incident on the first substrate 20 of the substrate coupling body. The laser L incident on the first substrate 20 may transmit the first substrate 20 and may reach the adhesive layer 40. The laser L transmitted to the adhesive layer 40 may remove the adhesive layer 40 by ablation. The adhesive layer 40 may be completely removed or remain partially. The coupling force between the first substrate 20 and the second substrate 30 may be reduced as the adhesive layer 40 is removed.

In an exemplary embodiment that the first substrate 20 may be directly coupled to the second substrate 30 without the adhesive layer 40, the laser L incident on the first substrate 20 may transmit the first substrate 20 and may reach the interface between the first substrate 20 and the second substrate 30. The laser L transmitted to the interface may separate the first substrate 20 from the second substrate 30. In an exemplary embodiment, the laser L may reach the second substrate 30 adjacent the first substrate 20 and separate the first substrate 20 from the second substrate 30.

When the laser L is irradiated onto the adhesive layer 40 or the interface between the adhesive layer 40 and the second substrate 30, soot may be generated. The soot generated may remain on the first substrate 30. The amount of the soot generated may relate to the output of the laser L. For example, as the output of the laser L is increased, more soot may be generated. Accordingly, by detecting the degree of soot generated, the output of the laser L may be estimated. If the output of the laser L is excessive, the second substrate 30 may be damaged by the laser L. If the output of the laser L is insufficient, the coupling force between the first substrate 20 and the second substrate 30 is insufficiently degraded, and thus the first substrate 20 and the second substrate 30 might not be separated from each other without causing some damage to the second substrate 30. If an external force is applied to the substrate coupling body in a state where the coupling force between the first substrate 20 and the second substrate 30 is insufficiently degraded, the second substrate 30 may be damaged. According to an exemplary embodiment of the present invention, the degree of the soot generated may be detected using the optical property of the first substrate 20 separated from the second substrate 30 using the laser L. The output of the laser L may be adjusted using the measured optical property of the first substrate 20 so that the laser L has an appropriate power density to avoid causing some damage on the second substrate 30. Accordingly, it is possible to prevent the damage of the second substrate that may occur in the process of separating the first substrate 20 and the second substrate 30. The details thereof will be described later.

In S20, the first substrate 20 and the second substrate 30 are separated from each other and spaced apart from each other, as shown in FIG. 5. The first substrate 20 and the second substrate 30 may be separated from each other in the peeling region R1. An external force may be applied to separate the first substrate 20 and the second substrate 30 from each other, and the external force may be provided from the substrate peeling device 10. At least a portion of the adhesive layer 40 may remain coupled to the first substrate 20. The second substrate 30 separated from the first substrate 20 may be carried outside by a carrying equipment.

In S30, the optical property of the first substrate 20 (S30) may be measured in the conveyance region R2. Referring to FIG. 6, the optical property measurement unit 13 includes a light irradiation unit 13a and a light receiving unit 13b. The light irradiation unit 13a provides a test light T to the first substrate 20. The test light T permeates the first substrate 20 and the adhesive layer 40. The light irradiation unit 13a is arranged over the first substrate 20, and the light receiving unit 13b is arranged under the first substrate 20. For example, the first substrate 20 is arranged between the light irradiation unit 13a and the light receiving unit 13b.

The light receiving unit 13b may receive the test light T through the first substrate 20 or both the first substrate 20 and the adhesive layer 40. For example, the test light T permeates or pass through the first substrate 20 and the adhesive layer 40.

In S30, the measuring of the optical properties of the first substrate 20 further includes measuring the optical property of the first substrate 20 from the test light T that is received by the light receiving unit 13b. The optical property of the first substrate 20 that is measured by the optical property measurement unit 13 may be a light permeability of the first substrate 20. The light permeability is calculated by dividing the light intensity of the test light T that is received in the light receiving unit 13b by the light intensity of the test light T that is provided from the light irradiation unit 13a.

Referring to FIG. 7, in S40, the output of the laser L is adjusted to have a light permeability in a first reference range R1 based on the measured light permeability. If the output of the laser L is increased, the amount of soot generated in S20 is also increased and thus the light permeability of the first substrate 20 is reduced. If the output of the laser L is decreased, the amount of stood generated in S20 is also decreased and thus, the light permeability of the first substrate 20 is increased. The first reference range R1 includes a range of the light permeability, which corresponds to the output of the laser L that facilitates the separation of the first substrate 20 and the second substrate 30 from each other and prevents the damage of the second substrate 30.

For example, if the light permeability measured in S30 is in the first reference range R1, the output of the laser is kept without adjustment in S40. However, the output of the laser L is adjusted in S40 if the light permeability measured in S30 is out of the first reference range R1. For example, the output of the laser L is decreased if the light permeability measured in S30 is lower than the first reference range R1. The output of the laser L is increased if the light permeability measured in S30 is higher than the first reference range R1. Accordingly, the substrate peeling device 10 may be controlled to maintain the output of the laser L at an appropriate level based on the permeability of the first substrate 20 separated from the second substrate 30. The output of the laser L may be automatically adjusted using the control unit 12 based on the permeability of the first substrate 20, or may be manually adjusted based on the permeability of the first substrate 20.

As described above, in the method for peeling a substrate according to an exemplary embodiment of the present invention, the optical property of the first substrate 20 is measured to monitor the output of the laser L. The output of the laser L is adjusted based on the optical property of the first substrate 20 to have an appropriate range of the output of the laser L if the output of the laser L deviates from the proper range R1 as shown in FIG. 7. Accordingly, the first substrate 20 and the second substrate 30 may be separated from each other without causing damage to the second substrate 30, which may occur when the second substrate 30 is separated from the first substrate 20 using the excessive or insufficient output of the laser L.

Figure 8:
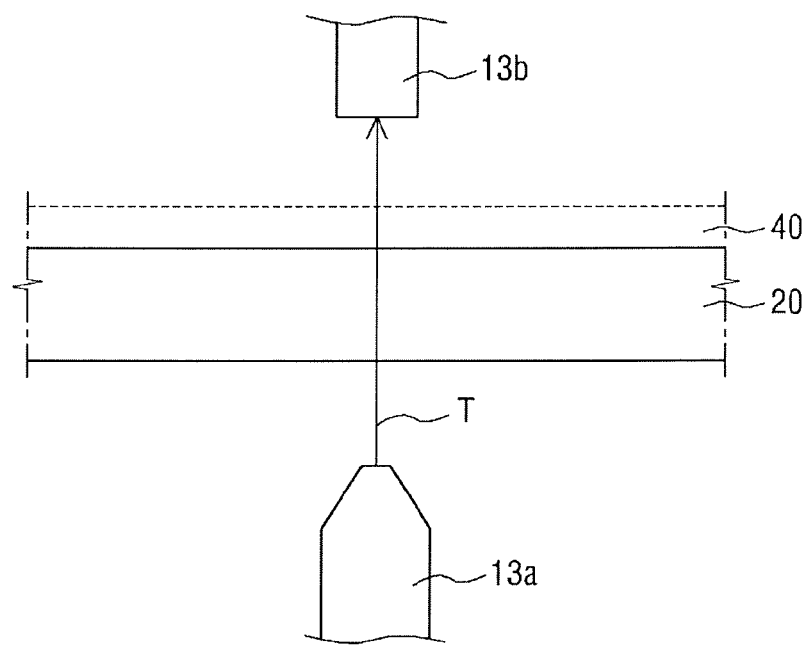
FIG. 8 is a view illustrating an arrangement for measuring an optical property of a first substrate according to an exemplary embodiment of the present invention.

Hereinafter, referring to FIG. 8, a method for peeling a substrate according to an exemplary embodiment of the present invention will be described. FIG. 8 shows an arrangement of the optical property measurement unit 13 measuring an optical property of a first substrate according to an exemplary embodiment of the present invention.

Referring to FIG. 8, the arrangement is substantially similar to that of FIG. 6, except that the light receiving unit 13b is arranged over the first substrate 20 and the light irradiation unit 13a is arranged under the first substrate 20. Using the arrangement of FIG. 8, the output of the laser is adjusted in a manner substantially similar to that described with reference to FIGS. 1 to 7, and thus the detailed description thereof will be omitted.

Figure 9:
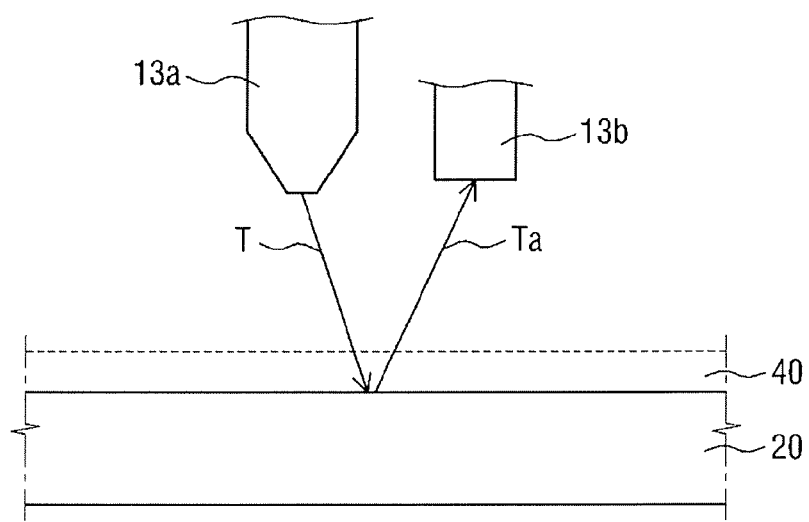
FIG. 9 is a view illustrating an arrangement for measuring an optical property of a first substrate according to an exemplary embodiment of the present invention.
Figure 10:
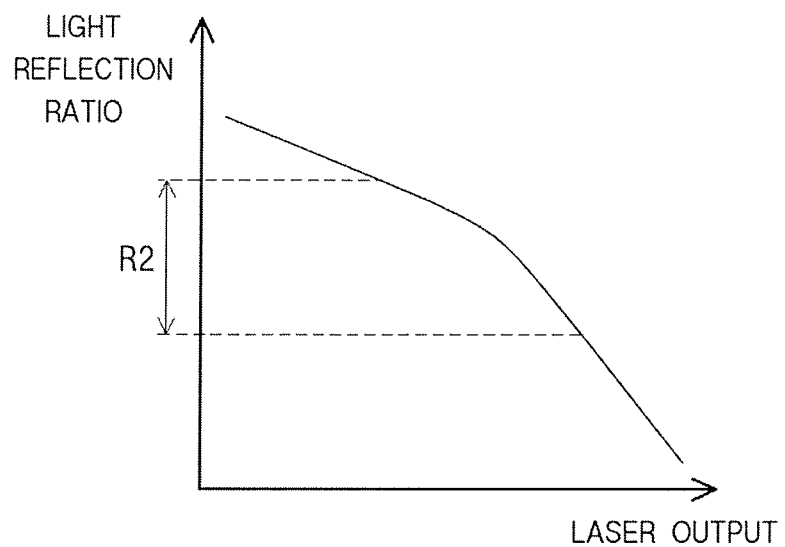
FIG. 10 is a graph illustrating a relationship between an intensity of a laser and a light reflection rate according to an exemplary embodiment of the present invention.

Hereinafter, referring to FIGS. 2, 3, 9 and 10, a method for peeling a substrate according to an exemplary embodiment of the present invention will be described. FIG. 10 is a graph illustrating a relationship between a laser output and a light reflection rate according to an exemplary embodiment of the present invention. FIG. 9 shows an arrangement of the optical property measurement unit 13 according to an exemplary embodiment. To measure a reflection ratio of the first substrate 20, the optical property measurement unit 13 provides test light T using a light irradiation unit 13a and receives light Ta reflected from the first substrate 20. The light irradiation unit 13a and the light receiving unit 13b are arranged over the first substrate 20 and in the same side of the substrate 20. The test light T may be reflected from a first surface of the first substrate 20 and the first surface is close to the adhesive layer 40, but is not limited thereto. The test light T may also be reflected from a second surface of the first substrate 20. The second surface is distant from the light irradiation unit 13a and opposite to the first surface. The test light T may also be reflected from the adhesive layer 40. The reflected test light Ta is received by the light receiving unit 13b. The light irradiation unit 13a and the light receiving unit 13b are formed separately, but are not limited thereto. The light irradiation unit 13a and the light receiving unit 13b may also be integrally formed.

For example, the reflection ratio is calculated by dividing the light intensity of the test light Ta that is received in the light receiving unit 13b by the light intensity of the test light T that is provided from the light irradiation unit 13a.

FIG. 10 shows a graph illustrating a relationship between the laser output and the light reflection rate according to an exemplary embodiment of the present invention. Referring to FIG. 10, if the output of the laser L is increased, the amount of soot generated in S20 is also increased and thus the amount of test light T that is absorbed by the soot is increased. Accordingly, the reflection ratio of the first substrate 20 is decreased. By contrast, if the output of the laser L is decreased, the reflection ratio is increased. A range of the light reflection ratio, which corresponds to the output of the laser L that facilitates the separation of the first substrate 20 and the second substrate 30 from each other and prevents damage of the second substrate 30, may include a second reference range R2.

For example, if the reflection ratio measured in S30 is in the second reference range R2, the output of the laser L may remain unchanged. However, if the reflection ratio measured in S30 is out of the second reference range R2, the output of the laser L may be adjusted. For example, if the light reflection ratio measured is lower than the second reference range R2, the output of the laser L is insufficient, and thus the substrate peeling device may be controlled to increase the output of the laser L to an appropriate level corresponding to the second reference range R2. If the light reflection ratio measured is greater than the second reference range R2, the output of the laser L is excessive, and thus the substrate peeling device 10 may be controlled to decrease the output of the laser L to the appropriate level corresponding to the second reference range R2. Except for using the reflection ratio to monitor the output of the laser L, the adjustment of the output of the laser is performed in a manner substantially similar to that described with reference to FIGS. 1 to 7, and thus the detailed description thereof will be omitted.

Figure 11:
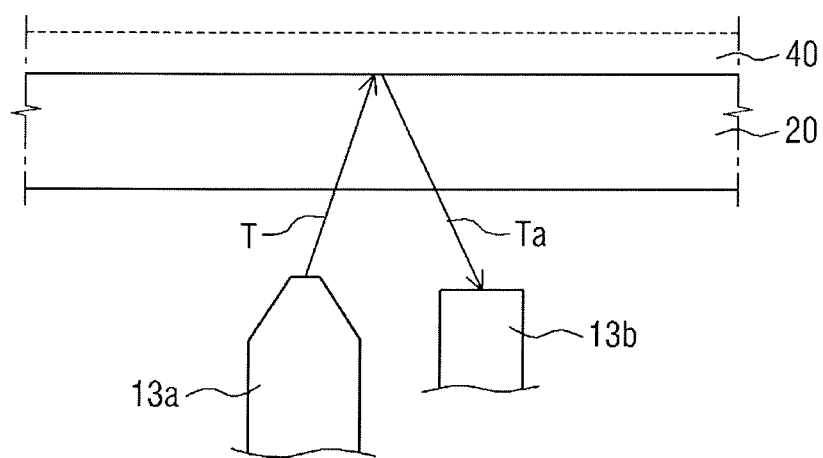
FIG. 11 is a view illustrating an arrangement for measuring an optical property of a first substrate according to an exemplary embodiment of the present invention.

Hereinafter, referring to FIGS. 2 and 11, a method for peeling a substrate according to an exemplary embodiment of the present invention will be described. FIG. 11 shows an arrangement of the optical property measurement unit 13 according to an exemplary embodiment. Referring to FIG. 11, the arrangement of the optical property measurement unit 13 is substantially similar to that of FIG. 9, except that the light irradiation unit 13a and the light receiving unit 13b are arranged under the first substrate 20. Using the arrangement of FIG. 11, the method for peeling a substrate as described above may be applied to the substrate coupling body and thus the detailed description thereof will be omitted.

Figure 12:
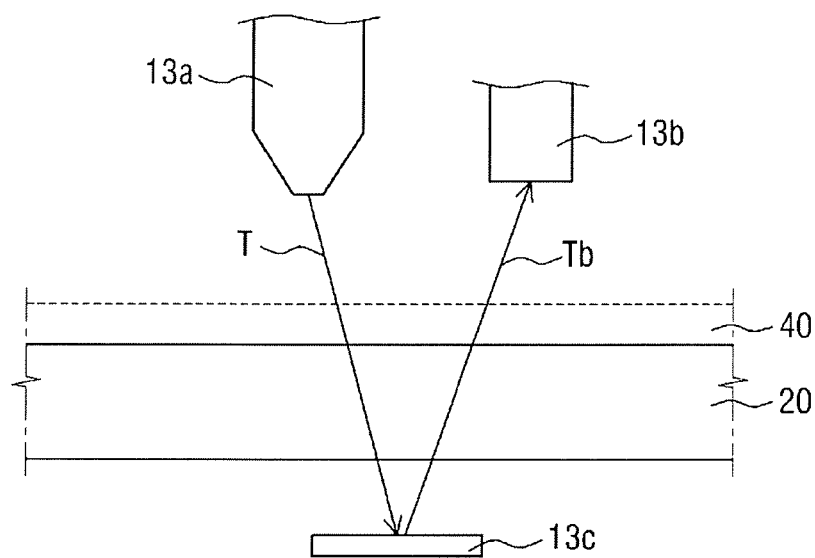
FIG. 12 is a view illustrating an arrangement for measuring an optical property of a first substrate according to an exemplary embodiment of the present invention.

Hereinafter, referring to FIGS. 2, 3, 4, 12 and 13, a method for peeling a substrate according to an exemplary embodiment of the present invention will be described. FIG. 12 shows an arrangement of the optical property measurement unit 13 to measure an optical property of the first substrate 20 according to an exemplary embodiment of the present invention, and FIG. 13 is a graph illustrating a relationship between the laser output and a retro reflection ratio according to an exemplary embodiment of the present invention.

Referring to FIG. 12, to measure the retro reflection ratio, the optical property measurement unit 13 provides a test light T to the first substrate 20 using a light irradiation unit 13a and receives a light Tb using a light receiving unit 13b. The light Tb is reflected by a reflection plate 13c arranged under the first substrate 20. The test light T and the reflected light Tb each permeate the first substrate 20 in an opposite direction from each other. The optical property measurement unit 13 may include the light irradiation unit 13a, the light receiving unit 13b, and the reflection plate 13c. The light irradiation unit 13a and the light receiving unit 13b may be formed separately or integrally. The light irradiation unit 13a and the light receiving unit 13b are arranged over the first substrate 20 and face the same side of the first substrate 20. The reflection plate 13c is arranged under the first substrate 20. In this case, the light irradiation unit 13a and the light receiving unit 13b may be arranged over the roller 15, and the reflection plate 13c may be arranged under the roller 15. The light irradiation unit 13a provides the test light T onto the first substrate 20. The test light T irradiated onto the upper portion of the first substrate 20 permeates the first substrate 20 and reaches the reflection plate 13c. The test light Tb reflected by the reflection plate 13c is provided to the substrate and permeates the first substrate 20. The test light Tb that permeates two times the first substrate 20 is received in the light receiving unit 13b.

The measuring of the optical property of the first substrate 20 may further include measuring the optical property of the first substrate 20 from the test light Tb that is received by the light receiving unit 13b. The optical property of the first substrate 20 measured by the optical property measurement unit 13 includes a retro reflection ratio. The retro reflection ratio is calculated by dividing the light intensity of the test light Tb that is received in the light receiving unit 13b by the light intensity of the test light T that is provided from the light irradiation unit 13a. Since the retro reflection ratio is calculated from the test light Tb that has passed through the first substrate 20 twice, the retro reflection ratio has a variation greater than the permeability calculated from the test light that has once permeated the first substrate 20, and thus the output levels of the laser L may be discriminated more precisely.

Figure 13:
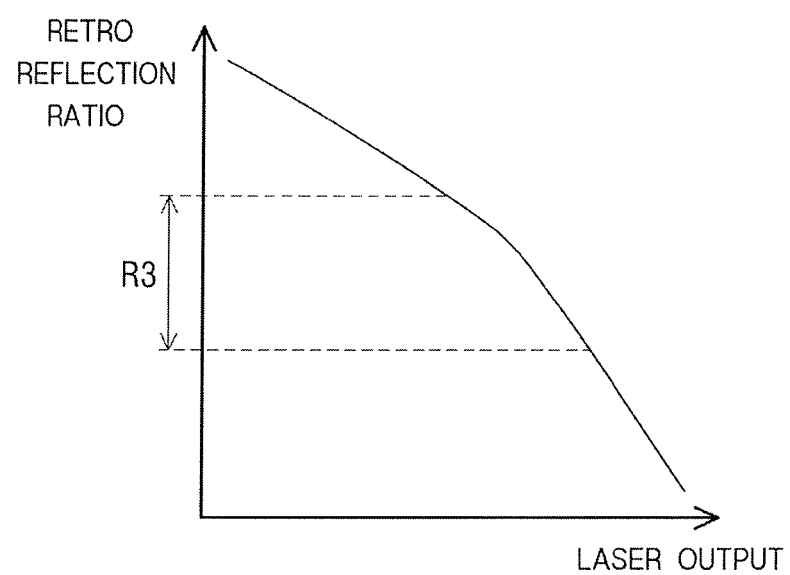
FIG. 13 is a graph illustrating a relationship between an intensity of a laser and a retro reflection ratio according to an exemplary embodiment of the present invention.

Referring to FIG. 13, the retro reflection ratio changes according to the output of the laser L. If the output of the laser L is increased, the amount of the stood generated in S30 is also increased and thus the retro reflection ratio of the first substrate 20 is decreased. If the output of the laser L is decreased, the amount of the stood generated in S30 is also decreased and thus the retro reflection ratio of the first substrate 20 is increased. The retro reflection ratio, which corresponds to an output of the laser L that facilitates the separation of the first substrate 20 and the second substrate 30 from each other and prevents damage of the second substrate 30, may have a third reference range R3. The adjustment of the output of the laser (S40) may include not changing the output of the laser L if the light permeability is in the third reference range R3. The adjustment of the output of the laser L may include increasing the output of the laser L if the retro reflection ratio exceeds the third reference range R3. Accordingly, in the case where the output of the laser L is insufficient, the substrate peeling device 10 may be controlled to maintain the output of the laser L within the third reference range R3. The adjustment of the output of the laser L may include decreasing the output of the laser L if the retro reflection ratio is lower than the third reference range R3. Accordingly, in the case where the output of the laser L is excessive, the substrate peeling device 10 may be controlled to maintain the output of the laser L within the third reference range R3. Except for using the retro reflection ratio to monitor the output of the laser L, the adjustment of the output of the laser is performed in a manner substantially similar to that described with reference to FIGS. 1 to 7, and thus the detailed description thereof will be omitted.

Figure 14:
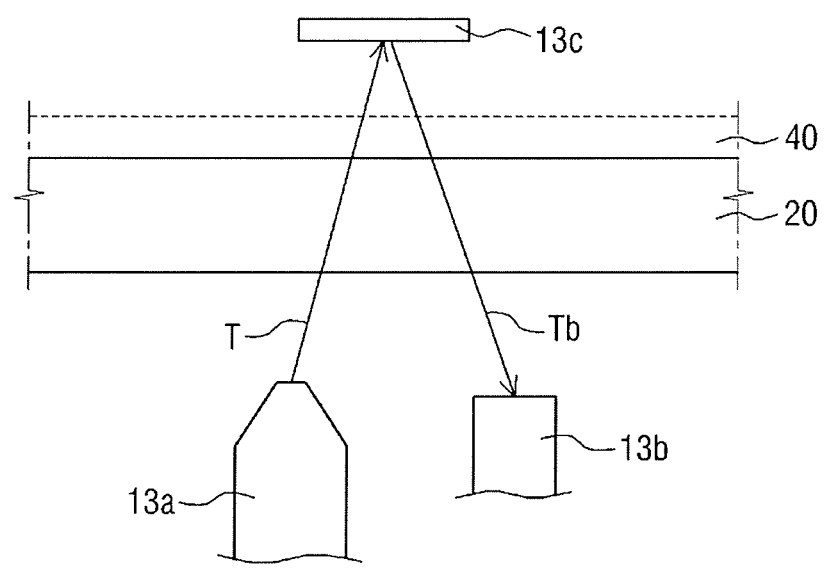
FIG. 14 is a view illustrating an arrangement for measuring an optical property of a first substrate according to an exemplary embodiment of the present invention.

Hereinafter, referring to FIGS. 2 and 14, a method for peeling a substrate according to an exemplary embodiment of the present invention will be described. FIG. 14 shows an arrangement of the optical property measurement unit 13 according to an exemplary embodiment. Referring to FIG. 14, the arrangement of the optical property measurement unit 13 is substantially similar to that of FIG. 12, except that the light irradiation unit 13a and the light receiving unit 13b are arranged under the first substrate 20 and the reflection plate 13c is arranged under the first substrate 20. Using the arrangement of FIG. 14, the method for peeling a substrate as described above may be applied to the substrate coupling body and thus the detailed description thereof will be omitted.

Figure 15:
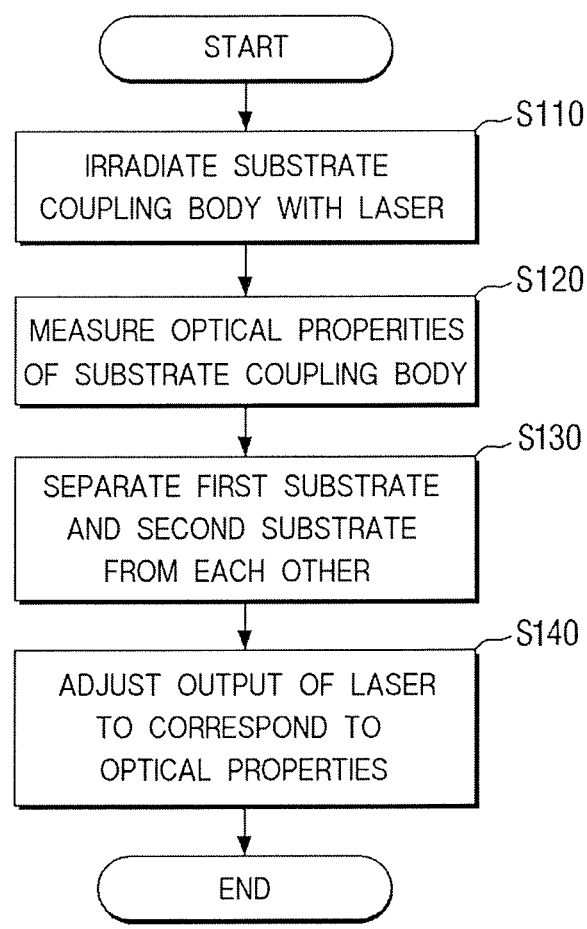
FIG. 15 is a flowchart illustrating a method for peeling a substrate according to an exemplary embodiment of the present invention.

Hereinafter, referring to FIGS. 15 and 16, a method for peeling a substrate according to an exemplary embodiment of the present invention will be described. FIG. 15 is a flowchart illustrating a method for peeling a substrate according to an exemplary embodiment of the present invention, and FIG. 16 shows an arrangement of measuring an optical property of a substrate coupling body according to an exemplary embodiment of the present invention.

Referring to FIG. 15, a method for peeling a substrate includes irradiating a substrate coupling body with laser (S110), measuring an optical property of the substrate coupling body (S120), separating a first substrate and a second substrate from each other (S130), and adjusting an output of the laser based on the optical property (S140). In the method for peeling a substrate, the irradiating the substrate coupling body with laser (S110) is substantially the same as the irradiating the substrate coupling body with the laser (S10) in FIG. 1, and the separating the first substrate and the second substrate from each other (S130) is substantially the same as the separating the first substrate and the second substrate from each other (S20) in FIG. 1.

Figure 16:
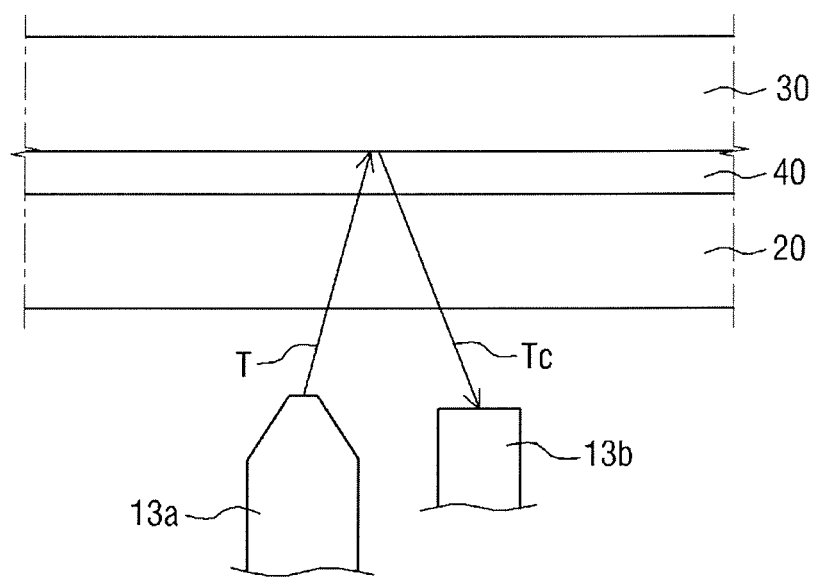
FIG. 16 is a view illustrating an arrangement for measuring an optical property of a substrate coupling body according to an exemplary embodiment of the present invention.

Referring to FIG. 16, the measuring the optical property of the substrate coupling body (S12) may include receiving a light which is provided to the first substrate 20 and is reflected by the substrate coupling body. The optical property measurement unit 13 includes a light irradiation unit 13a and a light receiving unit 13b which are arranged under the substrate coupling body. The light irradiation unit 13a and the light receiving unit 13b may be formed separately, but are not limited thereto. The light irradiation unit 13a and the light receiving unit 13b may also be integrally formed. Referring to FIGS. 2, 3, 15 and 16, the optical property measurement unit 13 may be arranged in the peeling region R1, and the substrate coupling body may be placed on the first stage 14. The light irradiation unit 13a provides test light T to the substrate coupling body so that the test light T is incident on the first substrate 20. The test light T may be reflected by the substrate coupling body. For example, the test light T is reflected from a first surface of the first substrate 20. The first surface is close to the adhesive layer 40. The test light T is also reflected by a second surface of the first substrate 20, the second substrate 30 and/or the adhesive layer 40. The second surface is opposite to the first surface and distant from the light receiving unit 13b receiving test light Tc that is reflected by the substrate coupling body.

The measuring of the optical property of the substrate coupling body (S120) may further include calculating the optical property of the substrate coupling body from the test light Tc that is received by the light receiving unit 13b. The optical property of the substrate coupling body that is measured by the optical property measurement unit 13 is a light reflection ratio. The light reflection ratio is calculated by dividing the light intensity of the test light Tc that is received in the light receiving unit 13b by the light intensity of the test light T that is provided from the light irradiation unit 13a.

A relationship between the light reflection ratio of the substrate coupling body and the output of the laser L may be substantially the same as the relationship between the light reflection ratio of the first substrate 20 and the output of the laser L. Since the explanation of the adjusting of the output of the laser L based on the optical property (S140) is substantially the same as the explanation of the adjusting of the output of the laser L to correspond to the optical property (S40) in FIG. 10, the explanation thereof will be omitted.

The separating of the first substrate 20 and the second substrate 30 from each other (S13) precedes the adjusting of the output of the laser L using the optical property (S140). Alternatively, the adjusting of the output of the laser L may be performed between the measuring of the optical property of the substrate coupling body (S120) and the separating of the first substrate 20 and the second substrate 30 (S130).

As described above, referring to FIGS. 1 to 16, the adjusting of the output of the laser to L based on the light permeability, the light reflection ratio, or the retro reflection ratio of the first substrate and the adjusting the output of the laser L based on the light reflection ratio of the substrate coupling body have been described. However, the optical property that is based on the adjustment of the output of the laser L is not limited thereto. For example, if the stood generated by the irradiation of the laser L has a specific color or the colors of the first substrate 20 and the second substrate 30 are changed due to the irradiation of the laser, the output of the laser L may be adjusted based on the color change of the test light T. Further, in the case where the refraction property of the test light may be changed according to the increase of the density of stood, the output of the laser L may be adjusted based on the change of the refraction property of the first substrate or the substrate coupling body.

Hereinafter, referring to FIGS. 17 to 24, a method for fabricating a flexible display device according to an exemplary embodiment of the present invention will be described.

Figure 17:
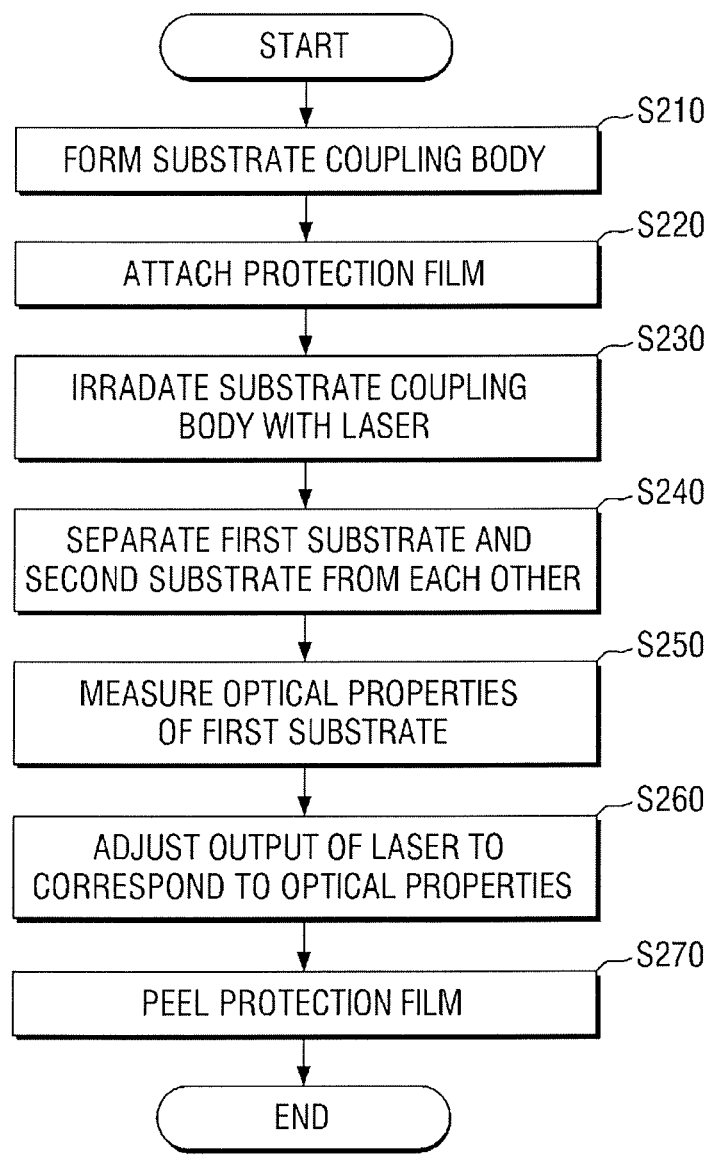
FIG. 17 is a flowchart illustrating a method for fabricating a flexible display device according to an exemplary embodiment of the present invention.

FIG. 17 is a flowchart illustrating a method for fabricating a flexible display device according to an exemplary embodiment of the present invention.

Referring to FIG. 17, a method for fabricating a flexible display device may include forming of a substrate coupling body (S210), attaching of a protection film to the substrate coupling body (S220), providing of a laser to the substrate coupling body (S230), separating of a first substrate and a second substrate from each other (S240), measuring of an optical property of the first substrate (S250), adjusting the output of the laser based on the optical property (S260), and peeling of the protection film (S270).

In the attaching of the protection film to the substrate coupling body (S220), first protection film is attached to the second substrate. If the protection 150 is attached to the second substrate, the protection film may support the second substrate after the separating the first substrate and the second substrate from each other (S240). Accordingly, the protection film may facilitate the process of fabricating the flexible display device after the second substrate is separated from the first substrate. The protection film may include plastic including polyethylene naphthalate, polyethylene terephthalate, polycarbonate, polyethersulfone, or metal foil including stainless steel (SUS).

In the peeling of the protection film (S270), the protection film may be separated from the second substrate. In an exemplary embodiment, the attaching of the protection film to the substrate coupling body (S220) and the peeling of the protection film (S270) may be omitted.

Figure 18:
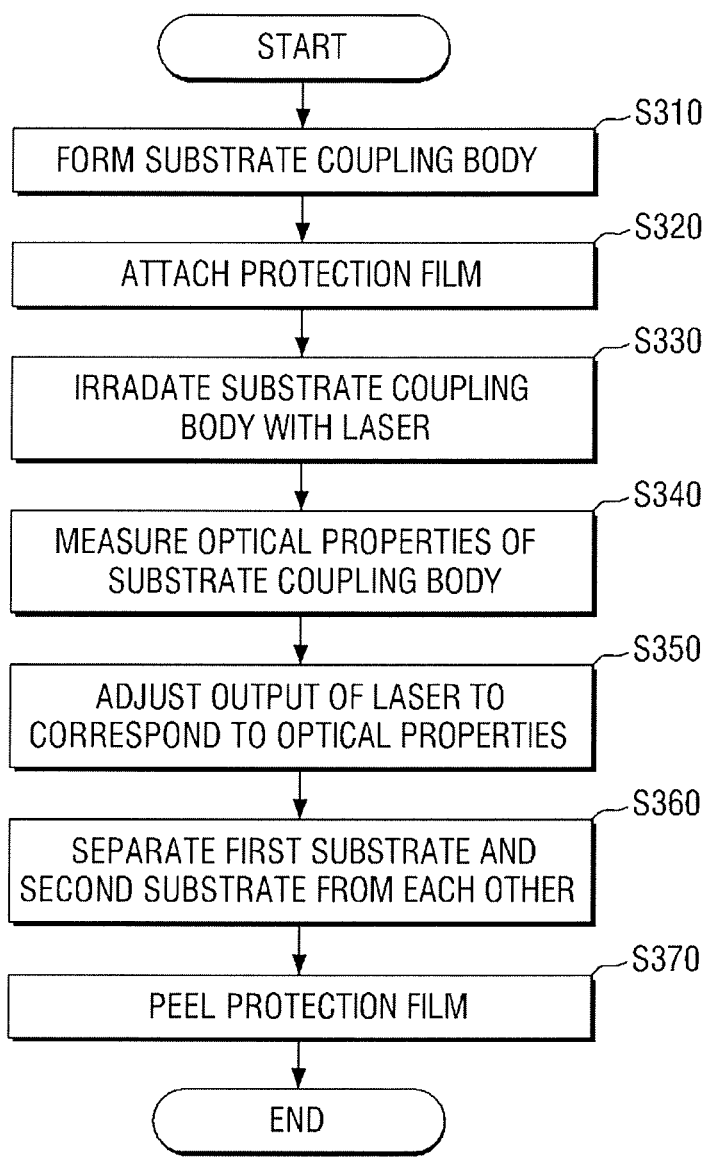
FIG. 18 is a flowchart illustrating a method for fabricating a flexible display device according to an exemplary embodiment of the present invention.

FIG. 18 is a flowchart illustrating a method for fabricating a flexible display device according to an exemplary embodiment of the present invention.

Referring to FIG. 18, a method for fabricating a flexible display device may include forming of a substrate coupling body (S310), attaching of a protection film (S320), providing of a laser to the substrate coupling body (S330), measuring of the optical property of the first substrate (S340), adjusting of the output of the laser based on the optical property (S350), separating of a first substrate and a second substrate from each other (S360), and peeling of the protection film (S370). Explanation of the forming the substrate coupling body (S310) is substantially the same as the explanation of the forming the substrate coupling body (S210) of FIG. 17, explanation of the attaching a protection film (S320) is substantially the same as the explanation of the attaching a protection film (S220) in FIG. 17, and the explanation of the irradiating the substrate coupling body with laser (S330) is substantially the same as the explanation of the irradiating the substrate coupling body with laser (S230) in FIG. 17. Further, the explanation of the separating a first substrate and a second substrate from each other (S360) is substantially the same as the explanation of the separating the first substrate and the second substrate from each other (S240) in FIG. 17, and the explanation of the peeling the protection film (S370) is substantially the same as the explanation of the peeling the protection film (S270) in FIG. 17. Accordingly, the explanation thereof will be omitted. In an exemplary embodiment, the attaching of the protection film to the substrate coupling body (S320) and the peeling of the protection film (S370) may be omitted.

The measuring of the optical property of the substrate coupling body (S340) may include receiving a light which is irradiated onto one surface of the first substrate and is reflected by the substrate coupling body. The optical property measurement unit includes a light irradiation unit and a light receiving unit. The light irradiation unit and the light receiving unit may be formed separately or integrally. The optical property measurement unit may be arranged in the peeling region. The light irradiation unit provides the test light to the first substrate. The test light is reflected by the substrate coupling body. For example, the test light may be reflected from the interface between the first substrate and the second substrate.

The measuring of the optical property of the substrate coupling body (S340) may further include calculating of the optical property of the first substrate from the test light that is received by the light receiving unit. The optical property of the substrate coupling body measured by the optical property measurement unit includes a light reflection ratio. The light reflection ratio is calculated by dividing the light intensity of the test light that is received in the light receiving unit by the light intensity of the test light that is emitted from the light irradiation unit.

A relationship between the light reflection ratio of the substrate coupling body and the output of the laser may be substantially the same as the relationship between the light reflection ratio of the first substrate and the output of the laser illustrated in FIG. 10. Since the explanation of the adjusting the output of the laser to correspond to the optical properties (S350) is substantially the same as the explanation of the adjusting the output of the laser to correspond to the optical properties (S40) in FIG. 1, the explanation thereof will be omitted.

While the present inventive concept has been shown and described with reference to exemplary embodiments thereof, it will be apparent to those of ordinary skill in the art that various changes in form and detail may be made therein without departing from the spirit and scope of the inventive concept as defined by the following claims.

What is claimed is:

1. A method of peeling a substrate, comprising:
providing a laser having a power density to a substrate coupling body, wherein the substrate coupling body includes a first substrate and a second substrate coupled to the first substrate;
separating the second substrate from the first substrate;
measuring an optical property of the first substrate separated from the second substrate; and
adjusting the power density of the laser based on the optical property of the first substrate,
wherein the optical property includes a light permeability of the first substrate, and the measuring the optical property of the first substrate comprises:
providing a test light to the first substrate so that the test light passes through the first substrate;
receiving the test light that has passed through the first substrate; and
calculating the light permeability of the first substrate from the received test light.

2. The method of claim 1, wherein the adjusting the power density of the laser comprises decreasing the power density of the laser if the light permeability is less than a predetermined reference range.

3. The method of claim 1, wherein the adjusting the power density of the laser comprises increasing the power density of the laser if the light permeability is greater than a predetermined reference range.

4. The method of claim 1, wherein the second substrate includes a flexible base material and a thin film transistor layer arranged on the flexible base material.

5. A method for peeling a substrate, comprising:
providing a laser having a power density to a substrate coupling body, wherein the substrate coupling body includes a first substrate and a second substrate coupled to the first substrate;
separating the second substrate from the first substrate;
measuring an optical property of the first substrate separated from the second substrate; and
adjusting the power density of the laser based on the optical property of the first substrate,
wherein the optical property includes a light reflection ratio, and the measuring the optical property of the first substrate comprises:
providing a test light to the first substrate so that the test light is reflected from the first substrate;
receiving the test light reflected from the first substrate; and
calculating the light reflection ratio using a first intensity of the test light provided to the first substrate and a second intensity of the test light reflected from the first substrate.

6. The method of claim 5, wherein the adjusting the power density of the laser comprises decreasing the power density of the laser if the light reflection ratio is less than a predetermined reference range.

7. The method of claim 5, wherein the adjusting the power density of the laser comprises increasing the power density of the laser if the light reflection ratio is greater than a predetermined reference range.

8. A method of peeling a substrate, comprising:
providing a laser having a power density to a substrate coupling body, wherein the substrate coupling body includes a first substrate and a second substrate coupled to the first substrate;
separating the second substrate from the first substrate;
measuring an optical property of the first substrate separated from the second substrate; and
adjusting the power density of the laser based on the optical property of the first substrate,
wherein the optical property includes a retro reflection ratio, and
the measuring the optical property of the first substrate comprises:
providing a test light to the first substrate so that the test light passes through the first substrate in a first direction;
reflecting the test light that has passed through the first substrate to the first substrate so that the test light reflected passes through the first substrate in a second direction opposite to the first direction;
receiving the test light that has passed through the first substrate in the second direction; and
calculating the retro reflection ratio from a first intensity of the test light provided to the first substrate and a second intensity of the test light that has passed through the first substrate in the second direction.

9. The method of claim 8, wherein the adjusting the power density of the laser comprises decreasing the power density of the laser if the retro reflection ratio is less than a predetermined reference range.

10. The method of claim 8, wherein the adjusting the power density of the laser comprises increasing the power density of the laser if the retro reflection ratio is greater than a predetermined reference range.

11. A method of fabricating a display device comprising:
providing a laser having a power density to a substrate coupling body, wherein the substrate coupling body includes a first substrate and a second substrate coupled to the first substrate;
measuring a reflection ratio of the substrate coupling body;
separating the first substrate and the second substrate from each other; and
adjusting the power density of the laser based on the reflection ratio.

12. The method of claim 11, wherein the laser is provided to a surface of the first substrate, and
the measuring of the reflection ratio of the substrate coupling body comprises:
providing a light to the substrate coupling body so that the light is reflected from the substrate coupling body;
receiving the light reflected from the substrate coupling body; and
calculating the reflection ratio from the received light.

13. The method of claim 12, wherein the power density of the laser is increased if the reflection ratio is less than a predetermined reference range.

14. The method of claim 12, wherein the power density of the laser is decreased if the reflection ratio is greater than a predetermined reference range.

15. The method of claim 11, wherein the second substrate includes a flexible base material and a thin film transistor layer arranged on the flexible base material.

16. The method of claim 15, further comprising attaching a first protection film to the second substrate before the laser is provided to the substrate coupling body.

17. The method of claim 16, further comprising attaching a second protection film to the second substrate after the first substrate and the second substrate is separated from each other.

18. The method of claim 17, further comprising removing the first protection film from the second substrate after the second protection film is coupled to the second substrate.

* * * * *